United States Patent
Satoh et al.

[11] Patent Number: 5,085,909
[45] Date of Patent: Feb. 4, 1992

[54] SQUARYLIUM COMPOUNDS AND OPTICAL INFORMATION RECORDING MEDIUM USING THE SAME

[75] Inventors: Tsutomu Satoh, Yokohama; Ikuo Shimizu; Yukiyoshi Ito, both of Yokkaichi, all of Japan

[73] Assignees: Ricoh Company, Ltd.; Kyowa Hakko Kogyo Co., Ltd., both of Tokyo, Japan

[21] Appl. No.: 495,715

[22] Filed: Mar. 16, 1990

Related U.S. Application Data

[63] Continuation-in-part of Ser. No. 341,325, Apr. 20, 1989, abandoned.

[30] Foreign Application Priority Data

Apr. 28, 1988 [JP] Japan .................................. 63-106944

[51] Int. Cl.$^5$ .................................................. B32B 3/02
[52] U.S. Cl. .......................................... 428/64; 428/65; 428/913; 369/288; 346/76 L; 346/135.1; 430/495; 430/948
[58] Field of Search ................... 430/495, 945; 428/64, 428/65, 913; 369/288; 346/76 L, 135.1

[56] References Cited

U.S. PATENT DOCUMENTS

4,673,630  6/1987  Katagiri et al. ......................... 430/72

FOREIGN PATENT DOCUMENTS

| | | |
|---|---|---|
| 1213462 | 11/1986 | Canada . |
| 1248804 | 1/1989 | Canada . |
| 1252667 | 4/1989 | Canada . |
| 187015 | 9/1986 | European Pat. Off. . |
| 310080 | 4/1989 | European Pat. Off. . |
| 60-41045 | 3/1985 | Japan . |
| 60-45253 | 3/1985 | Japan . |
| 60-120363 | 6/1985 | Japan . |
| 60-224674 | 9/1985 | Japan . |
| 60-262163 | 12/1985 | Japan . |
| 61-145143 | 7/1986 | Japan . |
| 61-185487 | 8/1986 | Japan . |
| 61-218550 | 9/1986 | Japan . |
| 61-218551 | 9/1986 | Japan . |
| 61-238755 | 10/1986 | Japan . |
| 61-260038 | 11/1986 | Japan . |
| 62-130890 | 6/1987 | Japan . |
| 62-290184 | 12/1987 | Japan . |
| 58-43460 | 1/1989 | Japan . |
| 1-110562 | 4/1989 | Japan . |
| 1-149890 | 6/1989 | Japan . |

Primary Examiner—Patrick J. Ryan
Attorney, Agent, or Firm—Cooper & Dunham

[57] ABSTRACT

Squarylium compounds having the following formula (I),

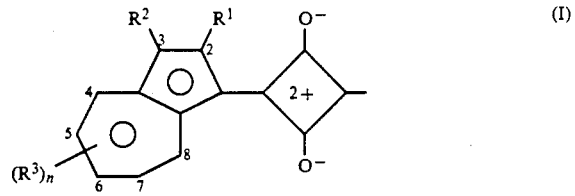

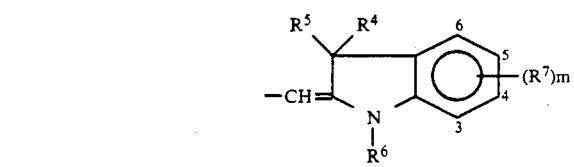

and an optical information recording medium comprising a substrate, and a recording layer formed on the substrate, comprising a squarylium compound having formula (II) are disclosed:

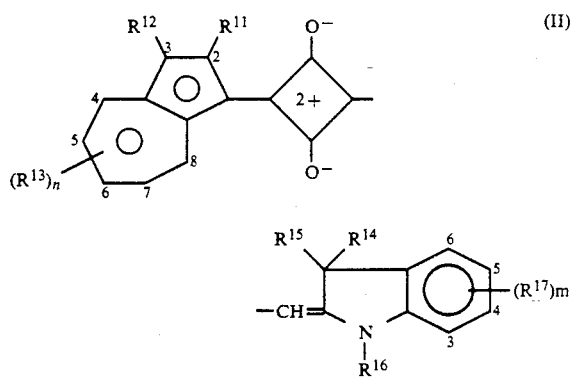

4 Claims, 4 Drawing Sheets

SQUARYLIUM COMPOUNDS AND OPTICAL INFORMATION RECORDING MEDIUM USING THE SAME

This application is a continuation-in-part of application Ser. No. 07/341,325, filed Apr. 20, 1989, now abandoned.

BACKGROUND OF THE INVENTION

1. Field of the Invention

This invention relates to squarylium compounds which absorb near infrared rays, and to an optical information recording medium using the same.

2. Discussion of Background

Materials which absorb near infrared rays have various uses, for instance, for (i) safe-light filters for photosensitive materials which are sensitive to infrared rays; (ii) infrared-light-cutting filters for controlling the growth of plants; (iii) materials for cutting heat rays of sunlight; (iv) infrared-light-cutting filters for protecting eye tissues from infrared rays; (v) infrared-light-cutting filters for light receiving elements of semiconductors.

In addition to the above, a recording material for use in an optical information recording medium is one of important uses of the near-infrared-rays-absorbing materials.

Hitherto, cyanine dyes such as phthalocyanine dyes; phenanthrene dyes; naphthoquinone dyes; and pyrylium dyes have been known as infrared-absorbing materials, and optical information recording media comprising such dyes have also been disclosed, for example, in Japanese Laid-open Patent Application 55-97033, 58-83344, 58-224793, 58-214162 and 59-24692.

Phthalocyanine dyes, however, are disadvantageous in that they have low photosensitivity and high decomposition temperatures, and are not readily vacuum-deposited. Further, since they have extremely low solubility in organic solvents, they cannot be coated by liquid coating.

Phenanthrene and naphthoquinone dyes are readily vacuum-deposited, but low in reflectance. The low reflectance causes a low contrast between a recorded area and a non-recorded area when recorded by laser beams. This will bring about inaccurate reproduction of recorded information.

Pyrylium and cyanine dyes are soluble in solvents, so that they can be coated by liquid coating. However, since these dyes have low light resistance, they are readily deteriorated by the light employed for the reproduction of recorded information.

SUMMARY OF THE INVENTION

Accordingly, a first object of the present invention is to provide compounds capable of highly absorbing near infrared rays, which are easily vacuum-deposited, and have high solubility in organic solvents, high preservation stability, high light resistance, high reflectance and high stability to the light employed for the reproduction of recorded information, and yield high C/N ratio when used in an optical information recording medium.

A second object of the present invention is to provide an optical information recording medium comprising such compounds, which has high reflectance, high preservation stability, high stability to the light employed for the reproduction of recorded information, and yields high contrast and high C/N ratio.

The first object of the invention can be attained by squarylium compounds represented by the following formula (I):

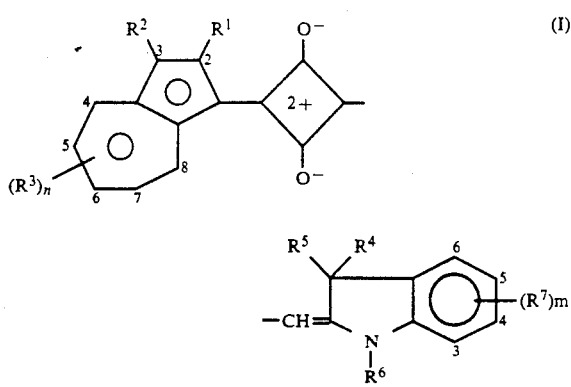

in which
R$^1$ and R$^2$ independently represent hydrogen, an alkyl group having 1 to 4 carbon atoms, an aralkyl group, or an aryl group, or R$^1$ and R$^2$ form an aromatic, heterocyclic or alkylene ring which may have a substituent, in combination with two adjacent carbon atoms in the ring to which R$^1$ and R$^2$ are bonded;

R$^3$ represents an alkyl group having 1 to 4 carbon atoms, an aralkyl group, an aryl group or an alkoxyl group having 1 to 4 carbon atoms; n is an integer of 0 to 3, and when n is 2 or 3, R$^3$s may be the same or different, or form an aromatic, heterocyclic or alkylene ring which may have a substituent, in combination with two adjacent carbon atoms in the ring to which R$^3$s are bonded;

R$^4$ and R$^5$ independently represent an alkyl group having 1 to 4 carbon atoms;

R$^6$ represents an alkyl group having 1 to 4 carbon atoms, an aralkyl group or an aryl group;

R$^7$ represents a halogen, an alkyl group having 1 to 4 carbon atoms, an aralkyl group, an aryl group or an alkoxyl group having 1 to 4 carbon atoms; m is an integer of 0 to 4, and when m is 2, 3 or 4, R$^7$s may be the same or different, or form an aromatic, heterocyclic or alkylene ring which may have a substituent, in combination with two adjacent carbon atoms in the ring to which R$^7$s are bonded.

The second object of the present invention can be achieved by an optical information recording medium comprising a substrate, and a recording layer formed on the substrate, which comprises any of the squarylium compounds represented by the following formula (II), when necessary, with an undercoat layer being interposed between the substrate and the recording layer and/or a protective layer being provided on the recording layer.

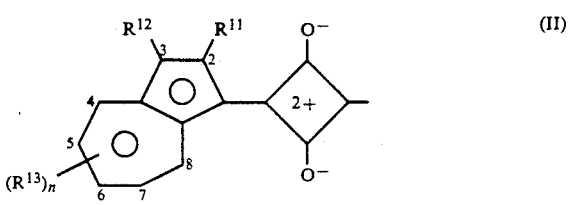

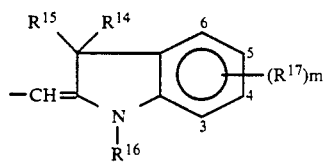

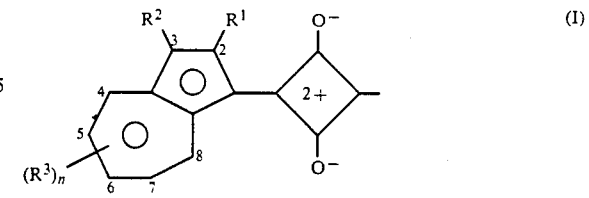

in which
R[11] and R[12] each represent hydrogen, an alkyl group having 1 to 8 carbon atoms, an aralkyl group, or an aryl group, or R[11] and R[12] form an aromatic, heterocyclic or alkylene ring which may have a substituent, in combination with two adjacent carbon atoms in the ring to which R[11] and R[12] are bonded;

R[13] represents an alkyl group having 1 to 8 carbon atoms, an aralkyl group, an aryl group or an alkoxyl group having 1 to 8 carbon atoms; l is an integer of 0 to 5, and when l is 2 to 5, R[13]s may be the same or different, or form an aromatic, heterocyclic or alkylene ring which may have a substituent, in combination with two adjacent carbon atoms in the ring to which R[13]s are bonded;

R[14] and R[15] each represent an alkyl group having 1 to 8 carbon atoms;

R[16] represents an alkyl group having 1 to 8 carbon atoms, an aralkyl group or an aryl group;

R[17] represents a halogen, an alkyl group having 1 to 8 carbon atoms, an aralkyl group, an aryl group or an alkoxyl group having 1 to 8 carbon atoms; m is an integer of 0 to 4, and when m is 2, 3 or 4, R[17]s may be the same or different, or form an aromatic, heterocyclic or alkylene ring which may have a substituent, in combination with two adjacent carbon atoms in the ring to which R[17]s are bonded.

DETAILED DESCRIPTION AND THE PREFERRED EMBODIMENTS

Figure 1:
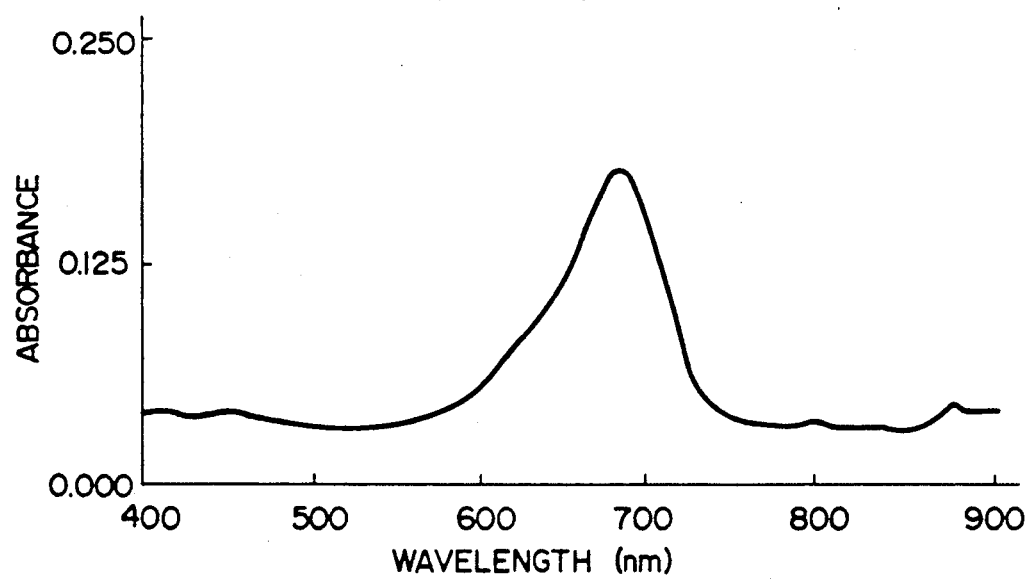
FIG. 1 is a spectroscopic characteristic chart of compound No. 1 according to the present invention prepared in Synthesis Example 1.

The squarylium compounds according to the present invention are represented by the following formula (I):

in which
$R^1$ and $R^2$ independently represent hydrogen, an alkyl group having 1 to 4 carbon atoms, an aralkyl group, or an aryl group, or $R^1$ and $R^2$ form an aromatic, heterocyclic or alkylene ring which may have a substituent, in combination with two adjacent carbon atoms in the ring to which $R^1$ and $R^2$ are bonded;

$R^3$ represents an alkyl group having 1 to 4 carbon atoms, an aralkyl group, an aryl group or an alkoxyl group having 1 to 8 carbon atoms; n is an integer of 0 to 3, and when n is 2 or 3, $R^3$s may be the same or different, or form an aromatic, heterocyclic or alkylene ring which may have a substituent in combination with two adjacent carbon atoms in the ring to which $R^3$s are bonded;

$R^4$ and $R^5$ independently represent an alkyl group having 1 to 4 carbon atoms;

$R^6$ represents an alkyl group having 1 to 4 carbon atoms, an aralkyl group or an aryl group;

$R^7$ represents a halogen, an alkyl group having 1 to 4 carbon atoms, an aralkyl group, an aryl group or an alkoxyl group having 1 to 4 carbon atoms; m is an integer of 0 to 4, and when m is 2, 3 or 4, $R^7$s may be the same or different, or form an aromatic, heterocyclic or alkylene ring which may have a substituent, in combination with two adjacent carbon atoms in the ring to which $R^7$s are bonded.

In the above formula (I), specific examples of the alkyl group represented by $R^1$, $R^2$, $R^3$, $R^4$, $R^5$, $R^6$ or $R^7$ are a methyl group, an ethyl group, a propyl group, an isopropyl group, a n-butyl group and an isobutyl group.

The alkyl moiety of the alkoxyl group represented by $R^3$ or $R^7$ is identical to that of the above alkyl groups, and specific examples of the alkoxyl group are a methoxy group, an ethoxy group, and an isopropoxy group.

The aralkyl group represented by $R^1$, $R^2$, $R^3$, $R^6$ or $R^7$ preferably contains 7 to 10 carbon atoms, and specific examples of the aralkyl group are a benzyl group, a phenylethyl group and a phenylpropyl group.

Specific examples of the aryl group represented by $R^1$, $R^2$, $R^3$, $R^6$ or $R^7$ are a phenyl group and a naphthyl group.

Specific examples of the halogen represented by $R^7$ are chlorine, bromine, and fluorine.

A typical example of the aromatic ring formed by $R^1$ and $R^2$, $R^3$s, or $R^7$s is a benzene ring.

Specific examples of the heterocyclic ring formed by $R^1$ and $R^2$, $R^3$s or $R^7$s are heterocyclic rings which contain oxygen, nitrogen or sulfur, with the moieties formed by $R^1$-$R^2$, $R^3$s or $R^7$s in the heterocyclic rings being —CH=CH—O—, =CH—O—CH=, —N=CH—S—, —CH=CH—S—, =CH—S—CH=, —S—CH=CH—, and —O—CH=CH—.

Examples of the moieties formed by $R^1$-$R^2$, $R^3$s or $R^7$s in the alkylene ring formed by $R^1$-$R^2$, $R^3$s or $R^7$s may have 3 or 4 carbon atoms, and examples of such an alkylene ring include propylene and butylene.

Examples of the substituents of the aromatic ring, the heterocyclic ring and the alkylene ring in the formula (I) are the same halogen, alkyl group, alkoxyl group, aralkyl group and aryl group as mentioned above.

The squarylium compounds according to the present invention can be prepared as follows:

Equimolar amounts of 3,4-dichloro-3-cyclobutene-1,2-dion and an azulene compound are allowed to react in a solvent with application of heat thereto. After completion of the reaction, the solvent is removed from the mixture, and a residual is hydrolyzed. The hydrolyzate is reacted with an equimolar amount of an indoline or indolium compound in a solvent while heating the reaction system, thereby preparing the desired squarylium compound. When an indolium compound is employed, the reaction is carried out in the presence of an equimolar amount of quinoline.

The scheme of the above reaction is as follows:

[Reaction Formula 1]

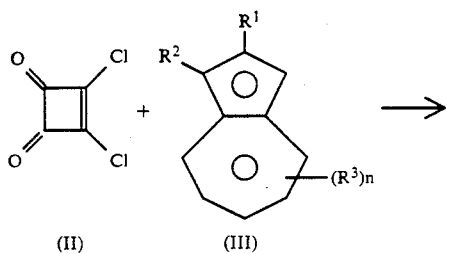

(II)    (III)

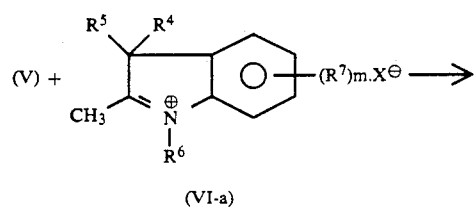

(IV)

[Reaction Formula 2]

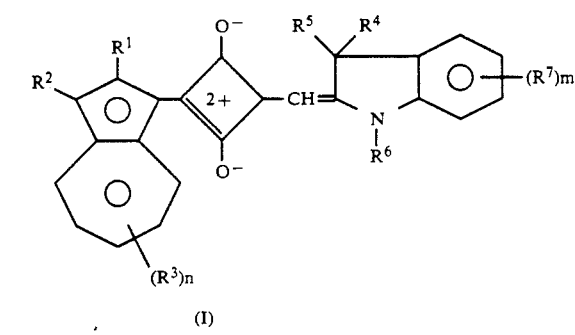

(V)

[Reaction Formula 3-a]

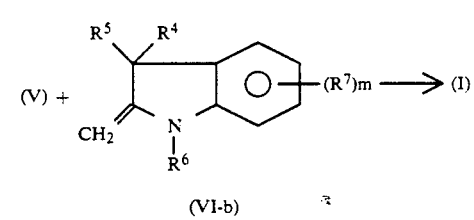

(VI-a)

(I)

[Reaction Formula 3-b]

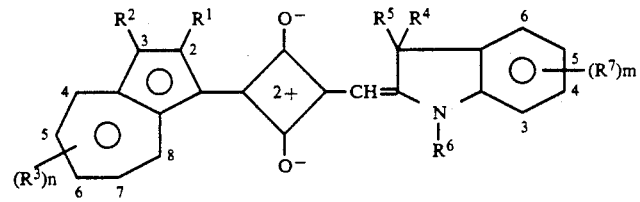

(VI-b)

Specific examples of the squarylium compounds according to the present invention are shown in Table 1.

TABLE 1

| No. | $R^1$ | $R^2$ | n | $R^3$ | $R^3$ | $R^3$ | $R^4$ | $R^5$ | $R^6$ | m | $R^7$ | $R^7$ |
|---|---|---|---|---|---|---|---|---|---|---|---|---|
| 1 | H | Me | 2 | 5-iPr | 8-Me |  | Me | Me | Me | 0 |  |  |
| 2 | H | Me | 2 | 5-iPr | 8-Me |  | Me | Me | Me | 1 | 5-Cl |  |
| 3 | H | Me | 2 | 5-iPr | 8-Me |  | Me | Me | Me | 2 | 5-A$_1$-6 |  |
| 4 | H | Me | 2 | 5-iPr | 8-Me |  | Me | Me | Bu | 0 |  |  |
| 5 | H | Me | 2 | 5-iPr | 8-Me |  | Et | Et | Et | 0 |  |  |
| 6 | H | Me | 2 | 5-iPr | 8-Me |  | Et | Et | Me | 0 |  |  |
| 7 | H | Me | 2 | 5-iPr | 8-Me |  | Me | Me | Bz | 1 | 5-OCH$_3$ |  |

TABLE 1-continued

![Structure diagram showing squarylium compound with indicated positions R¹, R², R³, R⁴, R⁵, R⁶, R⁷, and substituents (R⁵)n, (R⁷)m on the rings]

| No. | R¹ | R² | n | R³ | R³ | R³ | R⁴ | R⁵ | R⁶ | m | R⁷ | R⁷ |
|---|---|---|---|---|---|---|---|---|---|---|---|---|
| 8 | H | Me | 2 | 5-iPr | 8-Me | | Me | Me | Bz | 1 | 5-Cl | |
| 9 | H | Me | 2 | 5-iPr | 8-Me | | Me | Me | Bz | 2 | 5-A$_1$-6 | |
| 10 | H | Et | 3 | 4-Me | 6-Me | 8-Me | Me | Me | Me | 1 | 5-OCH$_3$ | |
| 11 | H | Me | 3 | 5-iPr | 7-Me | 8-Me | Me | Me | Me | 0 | | |
| 12 | iPr | Me | 2 | 4-Me | 8-Me | | Me | Me | Me | 0 | | |
| 13 | 2-A$_2$-3 | | 0 | | | | Me | Me | Me | 0 | | |
| 14 | 2=A$_3$=3 | | 0 | | | | Me | Me | Me | 0 | | |
| 15 | H | H | 2 | 4-A$_4$-5 | | | Me | Me | Me | 0 | | |
| 16 | H | H | 2 | 5-A$_4$-6 | | | Me | Me | Me | 0 | | |
| 17 | 2-A$_5$-3 | | 0 | | | | Me | Me | Me | 0 | | |
| 18 | 2-A$_6$-3 | | 0 | | | | Me | Me | Me | 0 | | |
| 19 | 2=A$_7$=3 | | 0 | | | | Me | Me | Me | 0 | | |
| 20 | 2-A$_8$-3 | | 0 | | | | Me | Me | Me | 0 | | |
| 21 | H | H | 2 | 4-A$_8$-5 | | | Me | Me | Me | 0 | | |
| 22 | H | Me | 3 | 5-iPr | 7-Ph | 8-Me | Me | Me | Me | 0 | | |
| 23 | 2-A$_1$-3 | | 1 | 6-OMe | | | Me | Me | Me | 0 | | |
| 24 | H | H | 3 | 4-Ph | 6-Ph | 8-Me | Me | Me | Me | 0 | | |
| 25 | H | H | 3 | 4-Me | 6-OMe | 8-Me | Me | Me | Me | 0 | | |
| 26 | H | H | 2 | 4-Ph | 8-Ph | | Me | Me | Me | 0 | | |
| 27 | H | H | 2 | 5-OMe | 7-OMe | | Me | Me | Me | 0 | | |
| 28 | Ph | Me | 0 | | | | Me | Me | Me | 0 | | |
| 29 | H | Me | 2 | 5-iPr | 8-Me | | Me | Me | Ph | 0 | | |
| 30 | H | Me | 2 | 5-iPr | 8-Me | | Me | Me | Et | 0 | | |
| 31 | H | iPr | 0 | | | | Me | Me | Me | 0 | | |
| 32 | H | Me | 2 | 5-iPr | 8-Me | | Me | Me | iPr | 0 | | |
| 33 | H | iPr | 0 | | | | Me | Me | Me | 2 | 5-A$_1$-6 | |
| 34 | H | iPr | 0 | | | | Me | Me | Ph | 0 | | |
| 35 | H | iPr | 0 | | | | Me | Me | Me | 1 | 5-Cl | |
| 36 | H | Me | 0 | | | | Me | Me | Me | 0 | | |
| 37 | H | Ph | 0 | | | | Me | Me | Me | 0 | | |
| 38 | H | iPr | 0 | | | | Me | Me | Et | 0 | | |
| 39 | H | iPr | 0 | | | | Me | Me | iPr | 0 | | |
| 40 | H | iPr | 0 | | | | Me | Me | Me | 1 | 5-Me | |
| 41 | H | Me | 0 | | | | Me | Me | Ph | 0 | | |
| 42 | H | Ph | 0 | | | | Me | Me | Ph | 0 | | |
| 43 | H | iPr | 0 | | | | Me | Me | Me | 2 | 3-Cl, 5-Cl | |
| 44 | H | iPr | 0 | | | | Me | Me | Ph | 2 | 5-A$_1$-6 | |
| 45 | H | iPr | 0 | | | | Me | Me | Me | 1 | 5-OCH$_3$ | |
| 46 | H | iPr | 0 | | | | Me | Me | A$_9$ | 0 | | |

In the above table, the following symbols respectively denote as follows:
Me ... Methyl group
Et ... Ethyl group
iPr ... Isopropyl group
Bu ... Butyl group
Bz ... Benzyl group
Ph ... Phenyl group
A$_1$... —CH=CH—CH=CH—
A$_2$... —CH=CH—O—
A$_3$... =CH—O—CH=
A$_4$... —O—CH=CH—
A$_5$... —N=CH—S—
A$_6$... —CH=CH—S—
A$_7$... =CH—S—CH=
A$_8$... —S—CH=CH—
A$_9$... 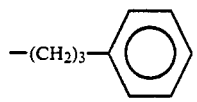

Not only the squarylium compounds of the present invention, but also the squarylium compounds of formula (II) are useful as recording materials for use in an optical information recording medium.

In the formula (II), the aryl group represented by $R^{11}$, $R^{12}$, $R^{13}$, $R^{16}$ or $R^{17}$, the halogen represented by $R^{17}$, the aromatic, heterocyclic or alkylene ring represented by $R^{11}$ and $R^{12}$, $R^{13}$s or $R^{17}$s and the substituents thereof are respectively the same as the aryl group, the halogen, the aromatic, heterocyclic or alkylene ring defined in formula (I).

The optical information recording medium according to the present invention comprises a substrate and a recording layer formed thereon comprising any of the squarylium compounds represented by the formula (II), and, if necessary, may further comprise an undercoat layer between the substrate and the recording layer, and a protective layer on the recording layer.

A pair of the above recording media can be airtightly fabricated into an air-sandwiched structure in which both recording layers are faced each other with an inner space therebetween, or a sandwiched structure in which both recording layers are faced each other with a protective layer therebetween.

Specific materials for each of the above layers of the optical information recording medium according to the present invention and the necessary properties for each layer will now be explained.

(1) Substrate

Only when recording of information and reproduction of recorded information are performed by application of laser beams to the side of the substrate, the substrate is required to be transparent to the laser beams.

As the materials for the substrate, plastics such as polyester, acrylic resin, polyamide resin, polycarbonate resin, polyolefine resin, phenol resin, epoxy resin and polyimide resin, glass, ceramics and metals can be employed.

On the surface of the substrate, preformats for address signals, and pregrooves serving as guide grooves may be formed, if necessary.

(2) Recording Layer

The recording layer comprises as the main component any of the squarylium compounds represented by the formula (II). When a laser beam is applied to the recording medium, the recording layer undergoes some optical changes. Thus, by application of a laser beam, information is recorded in the recording medium.

Compounds Nos. 1 to 46 shown in Table 1 are preferable examples of the recording material for use in the recording layer of the recording medium of the present invention.

In order to improve the recording characteristics and stability of the recording layer, dyes such as polymethine dyes, phthalocyanine dyes, tetrahydrocholine dyes, dioxazine dyes, triphenothiazine dyes, phenanthrene dyes, anthraquinone (indanthrene) dyes, cyanine (merocyanine) dyes, croconium dyes, xantene dyes, triarylmethane dyes, pyrylium dyes, indophenol dyes and azulene dyes; and metals and metallic compounds such as In, Sn, Te, Bi, Al, Se, $TeO_2$, SnO, As and Cd can be dispersed in the recording layer, or coated on the recording layer.

Further, polymeric materials; low molecular organic compounds, for instance, aminium compounds, imonium compounds and diimonium compounds, and low molecular inorganic complex compounds, for instance, bisdithiodiketone complexes and bisphenyldithiol complexes, which are capable of absorbing light having a longer wavelength than that of the light that can be absorbed by the squarylium compounds, can be incorporated into the recording layer.

Stabilizing agents such as metal complexes and phenol compounds, dispersing agents, flame retarders, lubricants and plasticizers are also usable in the recording layer when necessary.

The thickness of the recording layer is in the range of 100 Å to 10 μm, preferably 200 Å to 2 μm.

The recording layer can be formed on the substrate by any of known methods, for instance, vacuum deposition, chemical vapor deposition (CVD), sputtering, and liquid coating such as dip coating, spray coating, spinner coating, blade coating, roller coating and curtain coating.

(3) Undercoat Layer

An undercoat layer is formed between the substrate and the recording layer for the following purposes: (a) improvement of the adhesion between the substrate and the recording layer, (b) protection of the recording layer from water and gases, (c) improvement of the preservation stability of the recording layer, (d) improvement of the reflectance of the recording layer, (e) protection of the substrate from solvents, and (f) formation of pregrooves.

For the above purpose (a), a variety of polymeric materials such as ionomer resins, polyamide resins, vinyl resins, natural resins, natural polymeric materials, silicone and liquid rubber; and silane coupling agents can be employed.

For the purposes (b) and (c), inorganic compounds such as $BiO_2$, $MgF_2$, SiO, $TiO_2$, ZnO, TiN and SiN; and metals and metalloids such as Zn, Cu, S, Ni, Cr, Ge, Se, Au, Ag and Al can be used in addition to the above-described polymeric materials.

The purpose (d) can be achieved by using metals such as Al, Ag and Te; and organic thin layers having metallic gloss such as methine dyes and xanthene dyes.

For the purposes (e) and (f), it is preferable to employ ultraviolet ray-setting resins, thermosetting resins or thermoplastic resins.

(4) Protective Layer

A protective layer is formed on the recording layer for the purposes of (a) protecting the recording layer from being scratched, dusted and stained, (b) improving the preservation stability of the recording layer, and (c) improving the reflectance of the recording layer.

In order to achieve the above purposes, all the above-described materials for the undercoat layer are employable in the protective layer.

Stabilizing agents, dispersing agents, flame retarders, lubricants, anti-electrification agents, surface active agents and plasticizers can be incorporated both in the undercoat layer and the protective layer, if necessary. Further, the squarylium compounds of the present invention can also be incorporated in these two layers.

The squarylium compounds having formula (II) are readily vacuum-deposited. The compounds have high solubility in organic solvents, so that they can be subjected to solution coating. Further, they are highly soluble in polymeric materials, and have high preservation stability.

By using such squarylium compounds as a recording material, an optical information recording medium having high reflectance, capable of recording images with high contrast, and having high preservation and reproduction stabilities can be produced.

Other features of this invention will become apparent in the course of the following description of exemplary embodiments, which are given for illustration of the invention and are not intended to be limiting thereof.

Synthesis Example 1

To a mixture of 1.0 g of 3,4-dichloro-3-cyclobutene-1,2-dion and 30 ml of dichloromethane, 1.3 g of guaiazulene was added at room temperature. After one-hour stirring, the dichloromethane was distilled away from the mixture by a rotary evaporator. To the residue, 27 ml of acetic acid and 7 ml of water were added, and the mixture was heated on an oil bath at 100° C. for 15 hours. Thereafter, the acetic acid and the water were distilled away from the mixture by a rotary evaporator, followed by addition of 60 ml of n-butanol and 1.2 g of 1,3,3-trimethyl-2-methylene indoline to the residue. The mixture was heated again on the oil bath at 100° C. for 1 hour, and then the solvent and generated water were removed by a rotary evaporator. The residual product was purified by column chromatography, so that 1.4 g of compound No. 1 according to the present invention represented by the following formula No. 1, having a melting point of 239° to 240° C., was obtained.

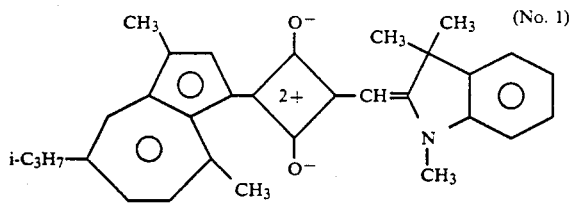

(No. 1)

The results of the elementary analysis of the thus obtained compound No. 1 were as follows:

|  | % C | % H | % N |
|---|---|---|---|
| Calculated | 82.82 | 6.95 | 3.12 |
| Found | 82.78 | 6.93 | 3.18 |

The above calculation was based on the formula for the compound No. 1 of $C_{31}H_{31}$; $NO_2$.

A spectroscopic characteristic chart of this compound is shown in FIG. 1 ($\lambda_{max}$: 684 nm, log$\epsilon$: 5.0, solvent: $CHCl_3$). The chart indicates that this compound has a large absorption peak in a near infrared region.

SYNTHESIS EXAMPLE 2

Synthesis Example 1 was repeated except that 1.2 g of 1,3,3-trimethyl-2-methylene indoline employed in Synthesis Example 1 was replaced with 1.5 g of 5-chloro-1,3,3-trimethyl-2-methylene indoline, whereby 1.0 g of compound No. 2 according to the present invention represented by the following formula No. 2, having a melting point of 250° to 51° C., was prepared.

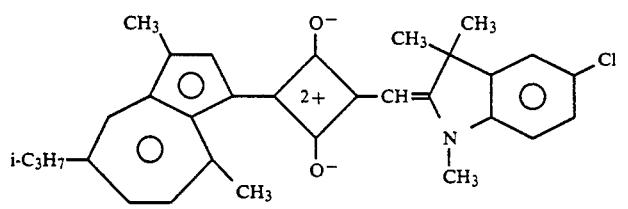

(No. 2)

The results of the elementary analysis of the thus obtained compound No. 2 were as follows:

|  | % C | % H | % N |
|---|---|---|---|
| Calculated | 76.92 | 6.25 | 2.89 |
| Found | 76.85 | 6.17 | 2.93 |

The above calculation was based on the formula for the compound No. 2 of $C_{31}H_{30}ClNO_2$.

Figure 2:
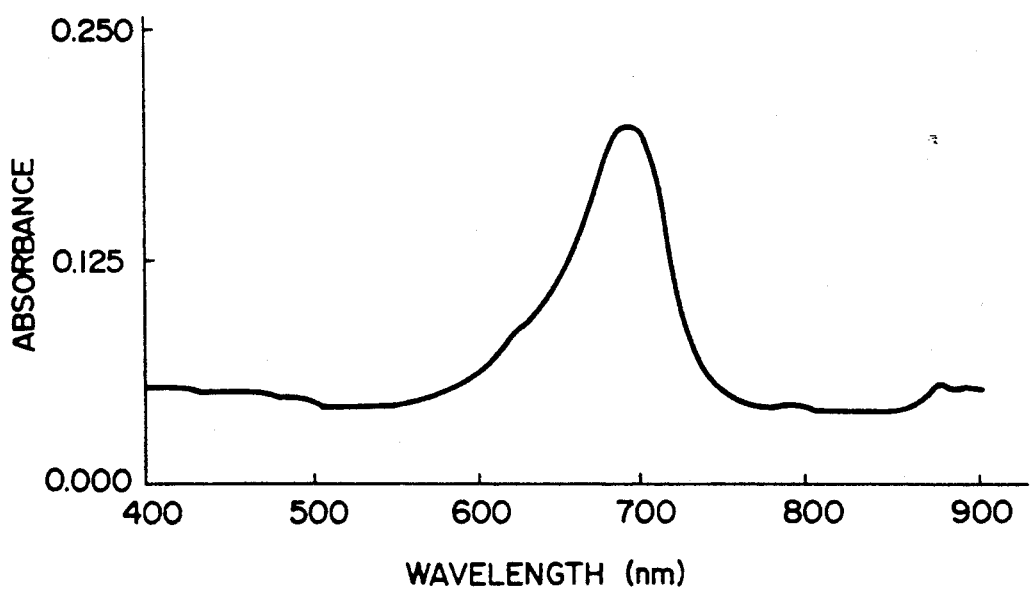
FIG. 2 is a spectroscopic characteristic chart of compound No. 2 according to the present invention prepared in Synthesis Example 2.

A spectroscopic characteristic chart of this compound is shown in FIG. 2 ($\lambda_{max}$: 690 nm, log$\epsilon$: 5.11, solvent: $CHCl_3$). The chart indicates that this compound has a large absorption peak in a near infrared region.

SYNTHESIS EXAMPLE 3

To a mixture of 1.3 g of 3,4-dichrolo-3-cyclobutene-1,2-dion and 30 ml of dichloromethane, 1.7 g of guaiazulene was added at room temperature. After one-hour stirring, the dichloromethane was distilled away from the mixture by a rotary evaporator. To the residue, 34 ml of acetic acid and 8 ml of water were added, and the mixture was heated on an oil bath at 100° C. for 15 hours. Thereafter, the acetic acid and the water were distilled away from the mixture by a rotary evaporator, followed by addition of 80 ml of n-butanol, 30 ml of toluene, 3.0 g of 1,1,2,3-tetramethyl-benz[e]-indolium iodide and 1.1 g of quinoline to the residue. The mixture was heated again on an oil bath at 100° C. for 3.5 hours, and then cooled. Insoluble materials were removed from the mixture by filtration, and the filtrate was concentrated by a rotary evaporator. The resulting product was purified by column chromatography, whereby 0.6 g of compound No. 3 according to the present invention represented by the following formula No. 3, having a melting point of more than 165° C., was obtained.

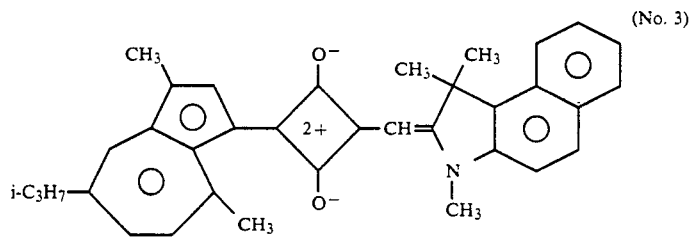

(No. 3)

The results of the elementary analysis of the thus obtained compound No. 3 were as follows:

|  | % C | % H | % N |
|---|---|---|---|
| Calculated | 84.13 | 6.66 | 2.80 |
| Found | 84.15 | 6.69 | 2.70 |

The above calculation was based on the formula for the compound No. 3 of $C_{35}H_{33}NO_2$.

Figure 3:
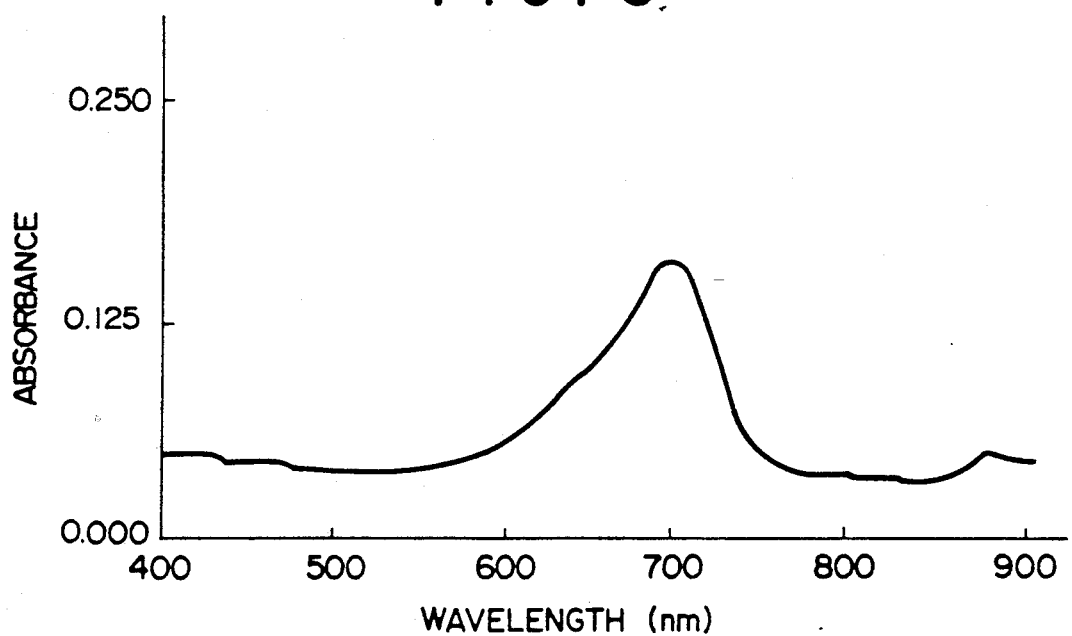
FIG. 3 is a spectroscopic characteristic chart of compound No. 3 according to the present invention prepared in Synthesis Example 3.

A spectroscopic characteristic chart of this compound is shown in FIG. 3 ($\lambda_{max}$: 699 nm, log$\epsilon$: 4.97, solvent: $CHCl_3$). The chart indicates that this compound has a large absorption peak in a near infrared region.

SYNTHESIS EXAMPLE 4

Synthesis Example 1 was repeated except that 1,3,3-trimethyl-2-methylene indoline employed in Synthesis Example 1 was replaced with 1-n-butyl-3,3-dimethyl-2-methylene indoline, whereby compound No. 4 according to the present invention represented by the following formula No. 4 was prepared.

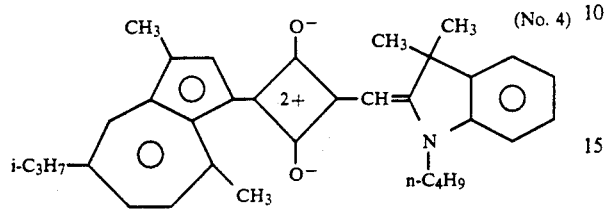

SYNTHESIS EXAMPLE 5

Synthesis Example 1 was repeated except that guaiazulene and 1,3,3-trimethyl-2-methylene indoline employed in Synthesis Example 1 were respectively replaced with 1-ethyl-4,6,8-trimethylazulene and 5-methoxy-1,3,3-trimethyl-2-methylene indoline, whereby compound No. 10 according to the present invention represented by the following formula No. 10 was prepared.

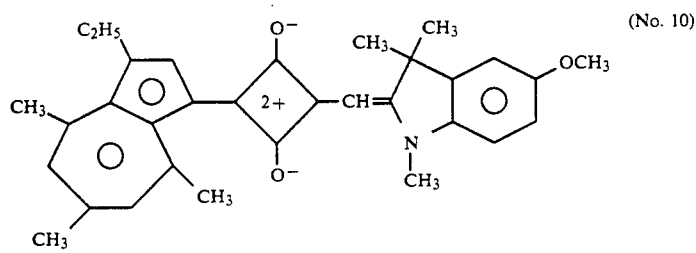

(No. 10)

SYNTHESIS EXAMPLE 6

Synthesis Example 1 was repeated except that guaiazulene employed in Synthesis Example 1 was replaced with azuleno[2,1-b]thiophene, whereby compound No. 20 according to the present invention represented by the following formula No. 20 was prepared.

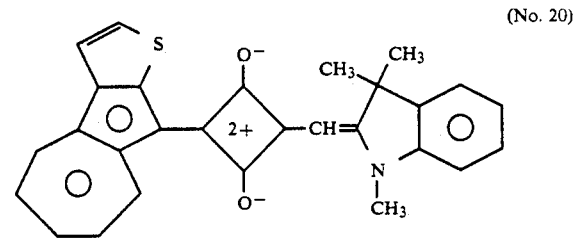

SYNTHESIS EXAMPLE 7

Synthesis Example 1 was repeated except that guaiazulene employed in Synthesis Example 1 was replaced with 4,6-diphenyl-8-methylazulene, whereby compound No. 24 according to the present invention represented by the following formula No. 24 was prepared.

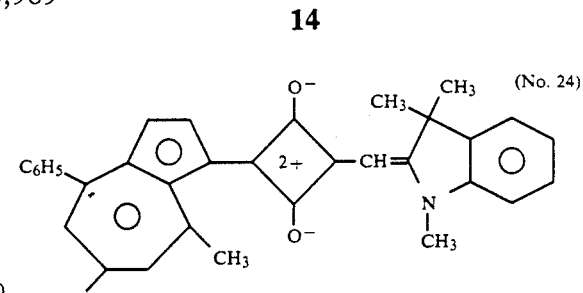

SYNTHESIS EXAMPLE 8

Synthesis Example 1 was repeated except that guaiazulene employed in Synthesis Example 1 was replaced with 6-methoxy-4,8-dimethylazulene, whereby compound No. 25 according to the present invention represented by the following formula No. 25 was prepared.

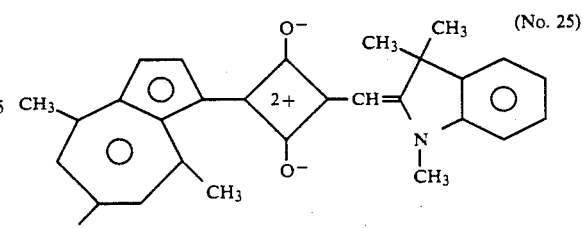

SYNTHESIS EXAMPLE 9

Synthesis Example 1 was repeated except that 1.2 g of 1,3,3-trimethyl-2-methylene indoline employed in Synthesis Example 1 was replaced with 1.6 g of 3,3-dimethyl-2-methylene-1-phenyl indoline, whereby 1.2 g of compound No. 29 according to the present invention represented by the following formula No. 29, having a decomposition point of 227° to 230° C., was prepared.

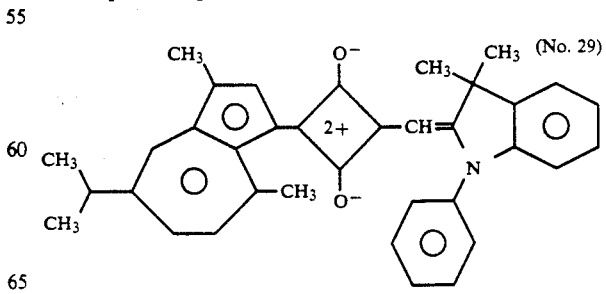

The results of the elementary analysis of the thus obtained compound No. 29 were as follows:

|  | % C | % H | % N |
|---|---|---|---|
| Calculated | 84.51 | 6.50 | 2.74 |
| Found | 84.30 | 6.48 | 2.70 |

The above calculation was based on the formula for the compound No. 29 of $C_{36}H_{33}NO_2$.

The spectroscopic characteristics of the compound determined by using chloroform are as follows:
$\lambda_{max}$: 695 nm
$\log\epsilon$: 5.1

SYNTHESIS EXAMPLE 10

Synthesis Example 1 was repeated except that 1.2 g of 1,3,3-trimethyl-2-methylene indoline employed in Synthesis Example 1 was replaced with 1.3 g of 1-ethyl-3,3-dimethyl- 2-methylene indoline, whereby 1.5 g of compound No. 30 according to the present invention represented by the following formula No. 30, having a melting point of 207° to 209° C., was prepared.

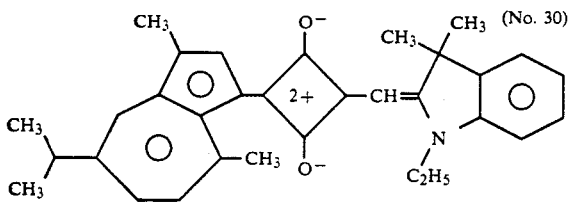
(No. 30)

The results of the elementary analysis of the thus obtained compound No. 30 were as follows:

|  | % C | % H | % N |
|---|---|---|---|
| Calculated | 82.91 | 7.17 | 3.02 |
| Found | 82.60 | 7.34 | 2.97 |

The above calculation was based on the formula for the compound No. 30 of $C_{32}H_{33}NO_2$.

The spectroscopic characteristics of the compound determined by using chloroform are as follows:
$\lambda_{max}$: 682 nm
$\log\epsilon$: 5.0

SYNTHESIS EXAMPLE 11

Synthesis Example 1 was repeated except that 1.3 g of guaiazulene employed in Synthesis Example 1 was replaced with 1.1 g of 1-isopropylazulene, whereby 1.5 g of compound No. 31 according to the present invention represented by the following formula No. 31, having a melting point of 239° to 242° C., was prepared.

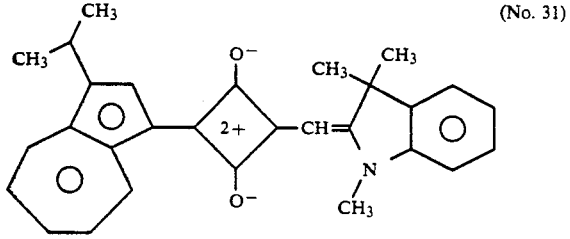
(No. 31)

The results of the elementary analysis of the thus obtained compound No. 31 were as follows:

|  | % C | % H | % N |
|---|---|---|---|
| Calculated | 82.63 | 6.46 | 3.32 |
| Found | 82.59 | 6.22 | 3.15 |

The above calculation was based on the formula for the compound No. 31 of $C_{29}H_{27}NO_2$.

The spectroscopic characteristics of the compound determined by using chloroform are as follows:
$\lambda_{max}$: 653 nm
$\log\epsilon$: 5.0

SYNTHESIS EXAMPLE 12

Synthesis Example 1 was repeated except that 1.2 g of 1,3,3,-trimethyl-2-methylene indoline employed in Synthesis Example 1 was replaced with 1.3 g of 3,3-dimethyl-2-methylene-1-isopropyl indoline, whereby 1.4 g of compound No. 32 according to the present invention represented by the following formula No. 32, having a melting point of less than 123° C., was prepared.

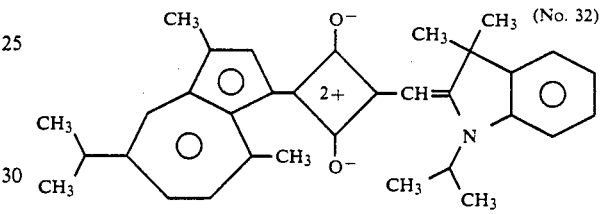
(No. 32)

The results of the elementary analysis of the thus obtained compound No. 32 were as follows:

|  | % C | % H | % N |
|---|---|---|---|
| Calculated | 82.98 | 7.39 | 2.93 |
| Found | 82.90 | 7.32 | 2.76 |

The above calculation was based on the formula for the compound No. 32 of $C_{33}H_{35}NO_2$.

The spectroscopic characteristics of the compound determined by using chloroform are as follows:
$\lambda_{max}$: 683 nm
$\log\epsilon$: 5.1

SYNTHESIS EXAMPLE 13

Synthesis Example 3 was repeated except that 1.7 g of guaiazulene employed in Synthesis Example 3 was replaced with 1.5 g of 1-isopropylazulene, whereby 2.3 g of compound No. 33 according to the present invention represented by the following formula No. 33, having a melting point of 285° to 289° C., was prepared.

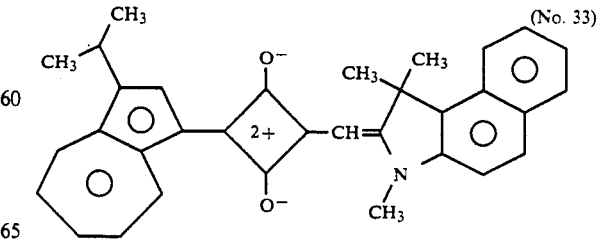
(No. 33)

The results of the elementary analysis of the thus obtained compound No. 33 were as follows:

|  | % C | % H | % N |
|---|---|---|---|
| Calculated | 84.05 | 6.20 | 2.97 |
| Found | 83.65 | 6.07 | 2.84 |

The above calculation was based on the formula for the compound No. 33 of $C_{33}H_{29}NO_2$.

The spectroscopic characteristics of the compound determined by using chloroform are as follows:

$\lambda_{max}$: 676 nm log$\epsilon$:5.0

SYNTHESIS EXAMPLE 14

Synthesis Example 1 was repeated except that 1.3 g of guaiazulene and 1.2 g of 1,3,3-trimethyl-2-methylene indoline employed in Synthesis Example 1 were respectively replaced with 1.1 g of 1-isopropylazulene and 1.6 g of 3,3-dimethyl-2-methylene-1-phenyl indoline, whereby 1.5 g of compound No. 34 according to the present invention represented by the following formula No. 34, having a decomposition point of 290° C., was prepared.

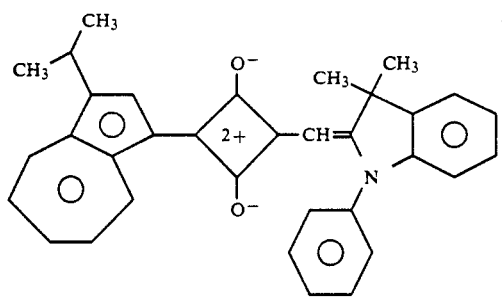
(No. 34)

The results of the elementary analysis of the thus obtained compound No. 34 were as follows:

|  | % C | % H | % N |
|---|---|---|---|
| Calculated | 84.44 | 6.04 | 2.90 |
| Found | 84.32 | 6.11 | 2.89 |

The above calculation was based on the formula for the compound No. 34 of $C_{34}H_{29}NO_2$.

The spectroscopic characteristics of the compound determined by using chloroform are as follows:

$\lambda$max: 670 nm log$\epsilon$: 5.1

SYNTHESIS EXAMPLE 15

Synthesis Example 1 was repeated except that 1.3 g of guaiazulene employed in Synthesis Example 1 was replaced with 1.4 g of 1-phenylazulene, whereby 1.0 g of compound No. 37 according to the present invention represented by the following formula No. 37, having a melting point of 240° to 245° C., was prepared.

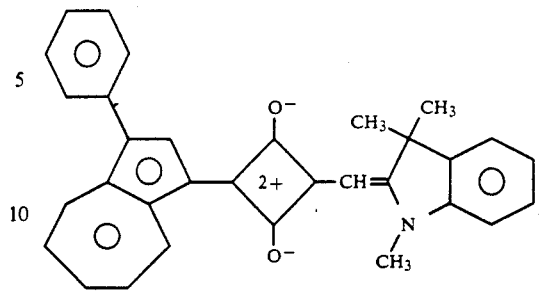
(No. 37)

The results of the elementary analysis of the thus obtained compound No. 37 were as follows:

|  | % C | % H | % N |
|---|---|---|---|
| Calculated | 84.37 | 5.53 | 3.07 |
| Found | 84.52 | 5.50 | 3.12 |

The above calculation was based on the formula for the compound No. 37 of $C_{32}H_{25}NO_2$.

The spectroscopic characteristics of the compound determined by using chloroform are as follows:

$\lambda_{max}$: 650 nm log$\epsilon$: 5.0

EXAMPLE 1

On an acrylic photopolymer layer having a thickness of 50 μm formed on a polymethyl methacrylate disk having a thickness of 1.2 mm and a diameter of 130 mm, a spiral guide groove having a pitch of 1.6 μm, a depth of 2000 Å and a half width of 0.4 μm was formed, whereby a substrate was prepared. A 0.8 wt. % 1,2-dichloroethane solution of compound No. 1 prepared in Synthesis Example 1 was spin-coated on the above-prepared substrate, and dried to form a recording layer having a thickness of approximately 800 Å, whereby recording medium No. 1 according to the present invention was prepared.

Figure 4:
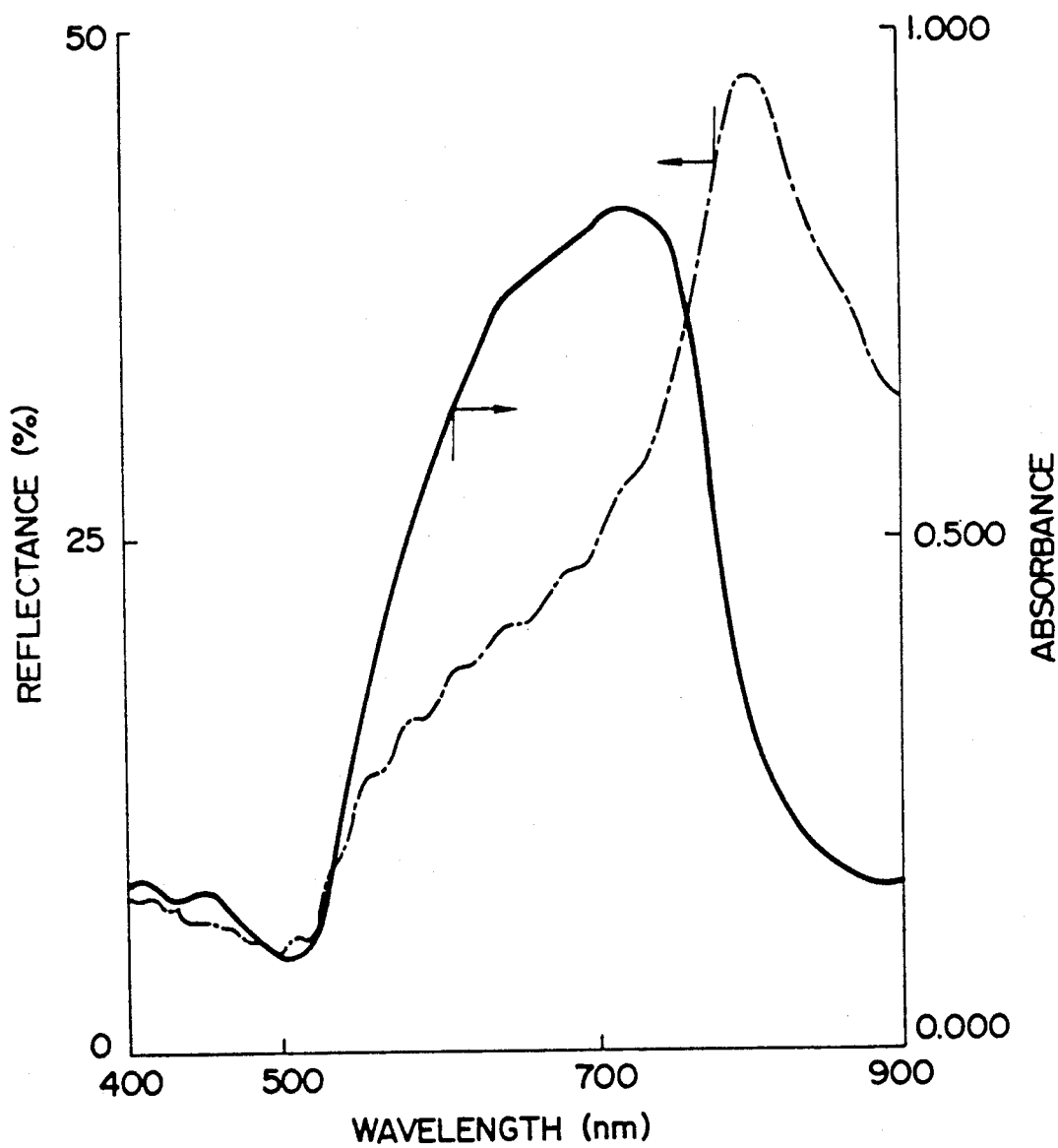
FIG. 4 is a chart showing the reflection and absorption curves of recording medium No. 1 according to the present invention prepared in Example 1.

FIG. 4 shows a spectroscopic characteristic chart of the thus prepared recording medium No. 1 obtained by applying parallel light beams to a smooth portion of the substrate of the above-prepared recording medium. The chart shows that the recording medium indicates high reflectance in a region of 780 to 830 nm, which corresponds to the wavelength range of semiconductor laser beams, which are currently used for optical disks.

In order to evaluate the recording characteristics of the recording medium, information was recorded from the substrate side by using a semiconductor laser beam having a beam diameter of 1.6 μm and a wavelength of 790 nm under the conditions of a recording frequency of 5 MHz, a line speed of 2.1 m/sec and a recording power of 3 mW.

By using the same semiconductor laser beam having a light intensity of 0.2 mW/cm², the recorded information was reproduced by detecting the light reflected from the recording medium. The detected light was subjected to a spectrum analysis (scanning filter 30 kHz) to determine the initial C/N ratio. Further, the reflectance (initial value) at a land portion of the guide groove was also determined by using the same semiconductor laser beams. The results are shown in Table 2.

Figure 5:
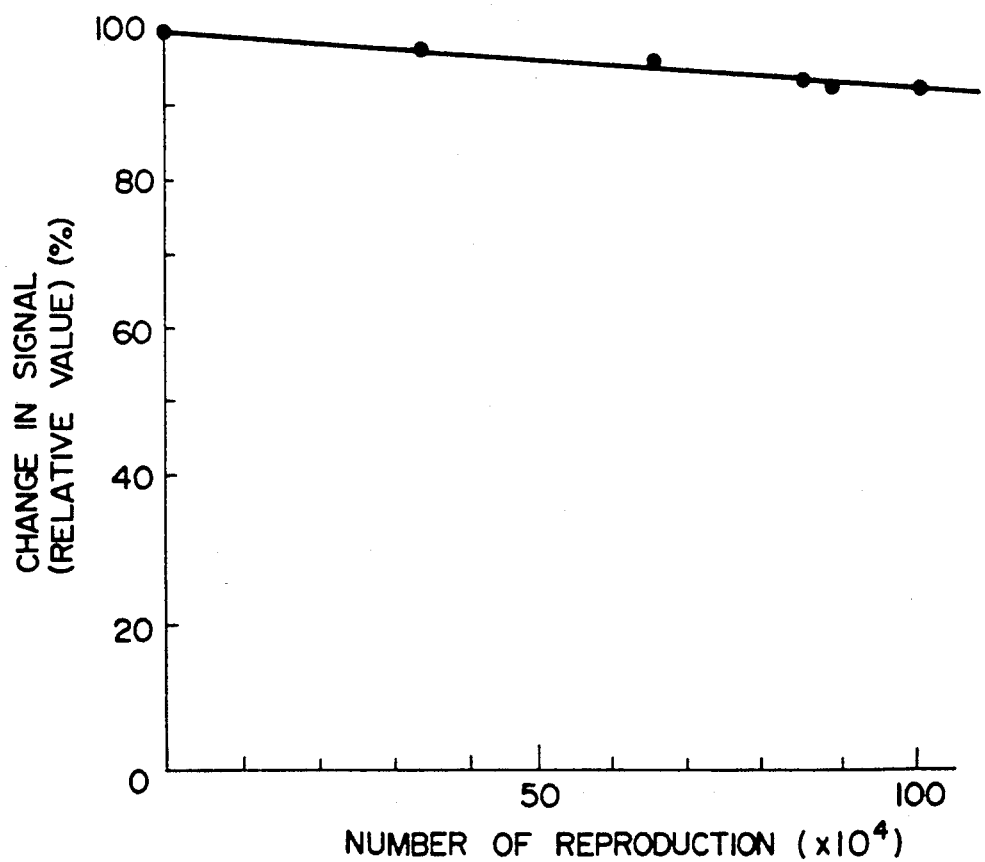
FIG. 5 is a graph showing the relationship between the reproduction number and the change in signals in recording medium No. 1 according to the present invention prepared in Example 1.

In order to evaluate the stability to the reproduction light, light having a light intensity of 0.25 mW/cm² was applied to the recording medium, and the recorded information was reproduced 1,000,000 times by using the same track. The change in the reflectance was converted to a change in signal. The results are shown in the graph in FIG. 5.

In addition to the above, the stability to the reproduction light was evaluated by conducting a reproduction deterioration acceleration test in which the recording medium was exposed to tungsten light of 54,000 lux for 10 hours, and then the reflectance and C/N ratio thereof were determined in the same manner as in the above. The results of this acceleration test are shown in Table 2.

The preservation stability of the recording medium was evaluated by carrying out an acceleration test in which the recording medium was allowed to stand at 60° C. and 90% RH for 800 hours, followed by determination of the reflectance and the C/N ratio thereof in the same manner as in the above. The results are shown in Table 2.

EXAMPLE 2

Example 1 was repeated except that compound No. 1 used in Example 1 as the recording material was replaced with compound No. 10 prepared in Synthesis Example 5, whereby recording medium No. 2 according to the present invention was prepared.

The recording characteristics of the recording medium were evaluated in the same manner as in Example 1. The results are shown in Table 2.

EXAMPLE 3

Example 1 was repeated except that compound No. 1 used in Example 1 as the recording material was replaced with compound No. 20 prepared in Synthesis Example 6, whereby recording medium No. 3 according to the present invention was prepared.

The recording characteristics of the recording medium were evaluated in the same manner as in Example 1. The results are shown in Table 2.

EXAMPLE 4

Example 1 was repeated except that compound No. 1 used in Example 1 as the recording material was replaced with compound No. 24 prepared in Synthesis Example 7, whereby recording medium No. 4 according to the present invention was prepared.

The recording characteristics of the recording medium were evaluated in the same manner as in Example 1. The results are shown in Table 2.

EXAMPLE 5

Example 1 was repeated except that compound No. 1 used in Example 1 as the recording material was replaced with compound No. 25 prepared in Synthesis Example 8, whereby recording medium No. 5 according to the present invention was prepared.

The recording characteristics of the recording medium were evaluated in the same manner as in Example 1. The results are shown in Table 2.

EXAMPLE 6

An injection-molded polycarbonate disk having a thickness of 1.2 mm and a diameter of 130 mm, with the same guide groove as in Example 1, formed by using a stamper capable of transferring a groove pattern identical to the guide groove in Example 1, was spin-coated with a 1 wt. % methanol-1,2-dichloroethane-butanol solution (weight ratio=8/1.5/0.5) of compound No. 3 prepared in Synthesis Example 3 to form a recording layer, whereby recording medium No. 6 according to the present invention was prepared.

Figure 6:
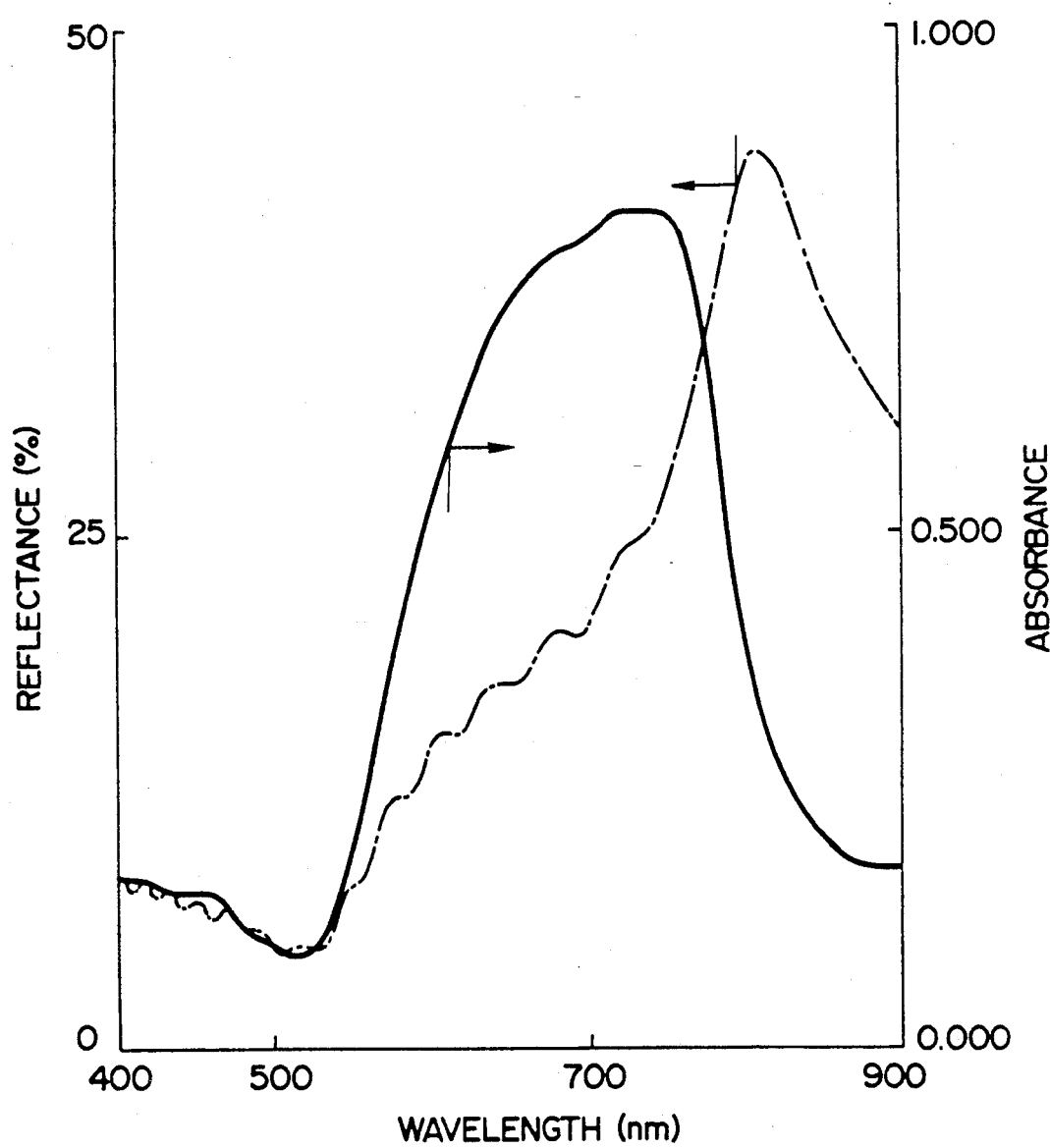
FIG. 6 is a chart showing the reflection and absorption curves of recording medium No. 6 according to the present invention prepared in Example 6.

FIG. 6 is a spectroscopic chart of the recording medium. The recording characteristics of the recording medium were evaluated in the same manner as in Example 1. The results are shown in Table 2.

EXAMPLE 7

Example 6 was repeated except that compound No. 3 used in Example 6 as the recording material was replaced with compound No. 2 prepared in Synthesis Example 2, whereby recording medium No. 7 according to the present invention was prepared.

The recording characteristics of the recording medium were evaluated in the same manner as in Example 1. The results are shown in Table 2.

EXAMPLE 8

Example 6 was repeated except that compound No. 3 used in Example 6 as the recording material was replaced with compound No. 4 prepared in Synthesis Example 4, whereby recording medium No. 8 according to the present invention was prepared.

The recording characteristics of the recording medium were evaluated in the same manner as in Example 1. The results are shown in Table 2.

EXAMPLE 9

Example 1 was repeated except that compound No. 1 used in Example 1 as the recording material was replaced with a mixture of compound No. 1 and a compound of the following formula (A) (weight ratio=1/1), whereby recording medium No. 9 according to the present invention was prepared.

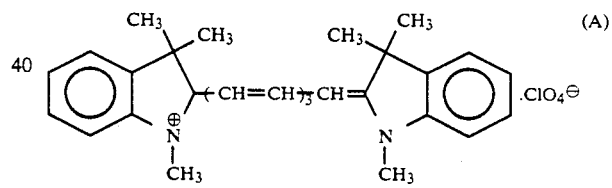

The recording characteristics of the recording medium were evaluated in the same manner as in Example 1. The results are shown in Table 2.

EXAMPLE 10

Example 1 was repeated except that compound No. 1 used in Example 1 as the recording material was replaced with a mixture of compound No. 1 and a compound of the following formula (B) (weight ratio=85/15), whereby recording medium No. 10 according to the present invention was prepared.

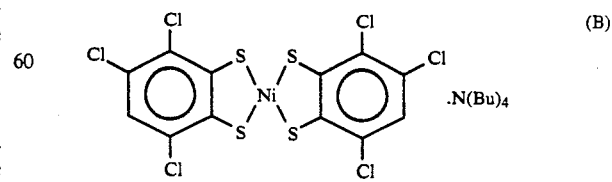

The recording characteristics of the recording medium were evaluated in the same manner as in Example 1. The results are shown in Table 2.

EXAMPLE 11

Example 1 was repeated except that compound No. 1 used in Example 1 as the recording material was replaced with a formula (C) (weight ratio=85/15), whereby recording medium No. 11 according to the present invention was prepared.

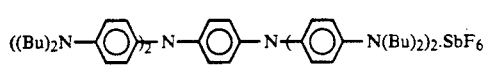

The recording characteristics of the recording medium were evaluated in the same manner as in Example 1. The results are shown in Table 2.

EXAMPLE 12

An injection-molded polycarbonate disk having a thickness of 1.2 mm and a diameter of 130 mm, with the same guide groove as in Example 1, formed by using a stamper capable of transferring a groove pattern identical to the guide groove in Example 1, was coated with a 25 wt. % butanol solution (Trademark "Colcoat N 103X" made by Colcoat Co., Ltd.), and dried for two hours to form an undercoat layer.

A 1 wt. % of methanol-1,2-dichloroethane-butanol solution (weight ratio=8/1.5/0.5) of compound No. 3 prepared in Synthesis Example 3 was spin-coated on the undercoat layer to form a recording layer, whereby recording medium No. 12 according to the present invention was prepared.

The recording characteristics of the recording medium were evaluated in the same manner as in Example 1. The results are shown in Table 2.

EXAMPLE 13

On a recording medium prepared in the same manner as in Example 1, silver was vacuum-deposited under a vacuum degree of $10^{-2}$ Torr to further form a protective layer, whereby recording medium No. 13 according to the present invention was prepared.

The recording characteristics of the recording medium were evaluated in the same manner as in Example 1. The results are shown in Table 2.

EXAMPLE 14

Example 1 was repeated except that compound No. 1 used in Example 1 as the recording material was replaced with compound No. 31 prepared in Synthesis Example 11, whereby recording medium No. 14 according to the present invention was prepared.

The recording characteristics of the recording medium were evaluated in the same manner as in Example 1. The results are shown in Table 2.

EXAMPLE 15

Example 1 was repeated except that compound No. 1 used in Example 1 as the recording material was replaced with compound No. 33 prepared in Synthesis Example 13, whereby recording medium No. 15 according to the present invention was prepared.

The recording characteristics of the recording medium were evaluated in the same manner as in Example 1. The results are shown in Table 2.

COMPARATIVE EXAMPLE 1

Example 1 was repeated except that compound No. 1 used in Example 1 as the recording material was replaced with a compound of the following formula (a), whereby comparative recording medium No. 1 was prepared.

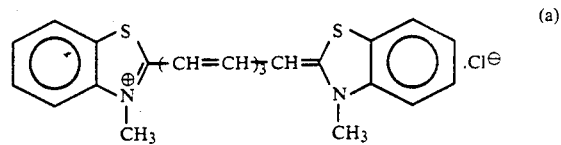

The recording characteristics of the recording medium were evaluated in the same manner as in Example 1. The results are shown in Table 2.

COMPARATIVE EXAMPLE 2

Example 1 was repeated except that compound No. 1 used in Example 1 as the recording material was replaced with a compound of the following formula (b), whereby comparative recording medium No. 2 was prepared.

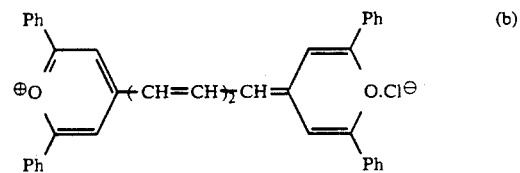

The recording characteristics of the recording medium were evaluated in the same manner as in Example 1. The results are shown in Table 2.

COMPARATIVE EXAMPLE 3

Example 1 was repeated except that compound No. 1 used in Example 1 as the recording material was replaced with a compound of the following formula (c), whereby comparative recording medium No. 3 was prepared.

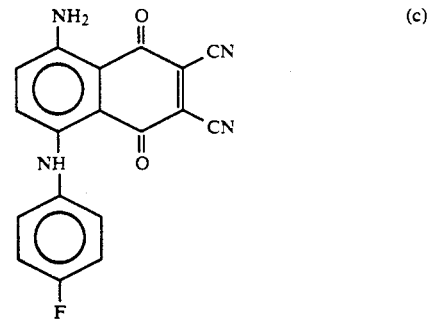

The recording characteristics of the recording medium were evaluated in the same manner as in Example 1. The results are shown in Table 2.

TABLE 2

| Recording Medium | Initial Value | | Reproduction-Deterioration Acceleration Test | | Preservation Stability Acceleration Test | |
|---|---|---|---|---|---|---|
| | R (%) | C/N (dB) | R (%) | C/N (dB) | R (%) | C/N (dB) |
| No. 1 | 31 | 56 | 23 | 53 | 28 | 54 |
| No. 2 | 31 | 56 | 21 | 51 | 26 | 53 |
| No. 3 | 29 | 57 | 22 | 53 | 26 | 53 |
| No. 4 | 29 | 57 | 24 | 54 | 27 | 54 |
| No. 5 | 30 | 56 | 23 | 53 | 27 | 53 |

TABLE 2-continued

| Recording Medium | Initial Value | | Reproduction-Deterioration Acceleration Test | | Preservation Stability Acceleration Test | |
|---|---|---|---|---|---|---|
| | R (%) | C/N (dB) | R (%) | C/N (dB) | R (%) | C/N (dB) |
| No. 6 | 26 | 57 | 16 | 48 | 25 | 55 |
| No. 7 | 27 | 57 | 18 | 50 | 26 | 56 |
| No. 8 | 28 | 56 | 15 | 48 | 26 | 55 |
| No. 9 | 26 | 55 | 15 | 49 | 25 | 54 |
| No. 10 | 29 | 55 | 27 | 54 | 26 | 53 |
| No. 11 | 28 | 54 | 27 | 52 | 27 | 53 |
| No. 12 | 32 | 57 | 22 | 53 | 28 | 54 |
| No. 13 | 29 | 50 | 26 | 47 | 27 | 47 |
| No. 14 | 36 | 53 | 31 | 52 | 29 | 51 |
| No. 15 | 38 | 55 | 32 | 54 | 28 | 51 |
| Comp. No. 1 | 23 | 55 | 10 | — | 18 | 49 |
| Comp. No. 2 | 18 | 54 | 7 | — | 15 | 43 |
| Comp. No. 3 | 15 | 53 | 14 | 53 | * | * |

In the above table, "R" denotes the reflectance; "—" denotes that the measurement was incapable; and "*" denotes that the measurement was incapable because the recording layer was crystallized during the preservation.

What is claimed is:

1. An optical information recording medium comprising a substrate, and a recording layer formed on said substrate, which comprises a squarylium compound having formula (II):

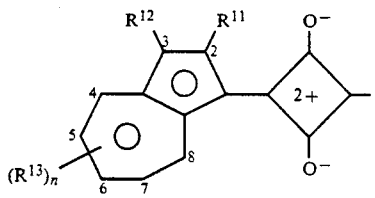

-continued

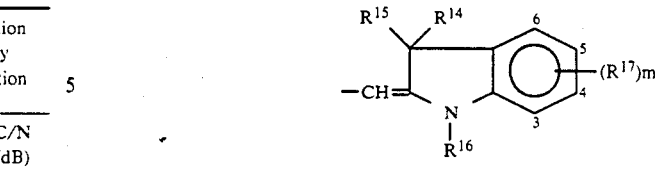

wherein
$R^{11}$ and $R^{12}$ each represent hydrogen, an alkyl group having 1 to 8 carbon atoms, an aralkyl group, or an aryl group, or $R^{11}$ and $R^{12}$ form an aromatic, heterocyclic or alkylene ring which may have a substituent, in combination with two adjacent carbon atoms in the ring to which $R^1$ and $R^{12}$ are bonded;

$R^{13}$ represents an alkyl group having 1 to 8 carbon atoms, an aralkyl group, an aryl group or an alkoxyl group having 1 to 8 carbon atoms; n is an integer of 0 to 5, and when n is 2 to 5, $R^{13}$s may be the same or different, or form an aromatic, heterocyclic or alkylene ring which may have a substituent, in combination with two adjacent carbon atoms in the ring to which $R^{13}$s are bonded;

$R^{14}$ and $R^{15}$ each represent an alkyl group having 1 to 8 carbon atoms;

$R^{16}$ represents an alkyl group having 1 to 8 carbon atoms, an aralkyl group or an aryl group;

$R^{17}$ represents a halogen, an alkyl group having 1 to 8 carbon atoms, an aralkyl group, an aryl group or an alkoxyl group having 1 to 8 carbon atoms; m is an integer of 0 to 4, and when m is 2, 3 or 4, $R^{17}$s may be the same or different, or form an aromatic, heterocyclic or alkylene ring which may have a substituent, in combination with two adjacent carbon atoms in the ring to which $R^{17}$s are bonded.

2. The optical information recording medium as claimed in claim 1, further comprising an undercoat layer between said substrate and said recording layer.

3. The optical information recording medium as claimed in claim 1, further comprising a protective layer on said recording layer.

4. The optical information recording medium as claimed in claim 1, wherein the thickness of said recording layer is in the range of of 100 Å to 10 μm.

* * * * *